(12) United States Patent
Oddsson et al.

(10) Patent No.: US 10,653,352 B2
(45) Date of Patent: *May 19, 2020

(54) FEEDBACK DEVICE FOR IMPROVED BALANCE CONTROL

(71) Applicant: RxFunction, Inc., Eden Prairie, MN (US)

(72) Inventors: Lars Oddsson, Edina, MN (US); Peter Meyer, Shrewsbury, MA (US)

(73) Assignee: RxFunction, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/522,195

(22) Filed: Jul. 25, 2019

(65) Prior Publication Data
US 2019/0374153 A1    Dec. 12, 2019

Related U.S. Application Data

(63) Continuation of application No. 16/358,146, filed on Mar. 19, 2019, now Pat. No. 10,390,751, which is a
(Continued)

(51) Int. Cl.
*A61B 5/00* (2006.01)
*A61B 5/103* (2006.01)
(Continued)

(52) U.S. Cl.
CPC .......... *A61B 5/4023* (2013.01); *A61B 5/1036* (2013.01); *A61B 5/1038* (2013.01); *A61B 5/1116* (2013.01); *A61B 5/1121* (2013.01); *A61B 5/4561* (2013.01); *A61B 5/486* (2013.01); *A61B 5/6807* (2013.01); *A61B 5/6829* (2013.01); *A61H 3/00* (2013.01); *A61N 1/36003* (2013.01); *G09B 19/003* (2013.01); *A61B 2562/0247* (2013.01);
(Continued)

(58) Field of Classification Search
CPC ... A61B 5/4023; A61B 5/1036; A61B 5/1038; A61B 5/1116; A61B 5/1121; A61B 5/4561; A61B 5/486; A61B 5/6807; A61B 5/6829
See application file for complete search history.

(56) References Cited

U.S. PATENT DOCUMENTS 4,569,352 A * 2/1986 Petrofsky .......... A61N 1/36003
607/49
4,745,930 A    5/1988 Confer et al.
(Continued)

*Primary Examiner* — Max F Hindenburg
(74) *Attorney, Agent, or Firm* — Davis, Brown, Koehn, Shors & Roberts, P.C.; Sean D. Solberg

(57) ABSTRACT

A feedback device for measuring pressure related information, and for providing that information in a way that is useful to the wearer of the device. At least one sensor detects pressure information and transmits at least one pressure information signal to a signal processing subsystem. The signal processing subsystem converts the received pressure information signal into at least one stimulation control signal. The signal processing subsystem then transmits the stimulation control signal to at least one stimulator, which provides stimulation to a wearer of the device reflecting the stimulation control signal received from the signal processing subsystem.

20 Claims, 12 Drawing Sheets

Related U.S. Application Data continuation of application No. 16/119,558, filed on Aug. 31, 2018, now abandoned, which is a continuation of application No. 15/966,152, filed on Apr. 30, 2018, which is a continuation of application No. 15/250,365, filed on Aug. 29, 2016, now Pat. No. 9,955,904, which is a continuation of application No. 15/052,349, filed on Feb. 24, 2016, now Pat. No. 10,178,970, which is a continuation of application No. 14/605,380, filed on Jan. 26, 2015, now Pat. No. 9,289,174, which is a continuation of application No. 14/568,398, filed on Dec. 12, 2014, now Pat. No. 9,402,580, which is a continuation of application No. 10/511,023, filed on Oct. 8, 2004, now Pat. No. 8,974,402.

(51) Int. Cl.
*A61B 5/11* (2006.01)
*A61H 3/00* (2006.01)
*A61N 1/36* (2006.01)
*G09B 19/00* (2006.01)
*A61H 23/02* (2006.01)

(52) U.S. Cl.
CPC ........ *A61B 2562/046* (2013.01); *A61H 23/02* (2013.01); *A61H 2201/0184* (2013.01); *A61H 2201/164* (2013.01); *A61H 2201/5061* (2013.01)

(56) References Cited

U.S. PATENT DOCUMENTS

| | | |
|---|---|---|
| 4,760,850 A | 8/1988 | Phillips et al. |
| 4,813,436 A | 3/1989 | Au et al. |
| 5,551,445 A | 9/1996 | Nashner et al. |
| 5,678,448 A | 10/1997 | Fullen et al. |
| 5,979,067 A | 11/1999 | Waters et al. |
| 6,063,046 A | 5/2000 | Allum et al. |
| 6,174,294 B1 | 1/2001 | Crabb et al. |
| 6,978,684 B2 | 12/2005 | Nurse et al. |
| 7,403,821 B2 | 7/2008 | Haugland et al. |
| 7,998,092 B2 | 8/2011 | Avni et al. |
| 8,974,402 B2 | 3/2015 | Oddsson et al. |
| 2002/0055779 A1 | 5/2002 | Andrews et al. |
| 2015/0123802 A1 | 5/2015 | Oddsson et al. |

* cited by examiner

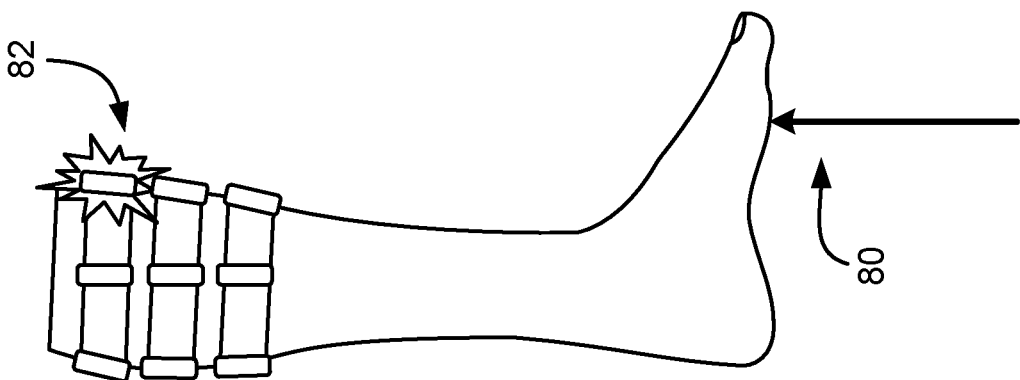
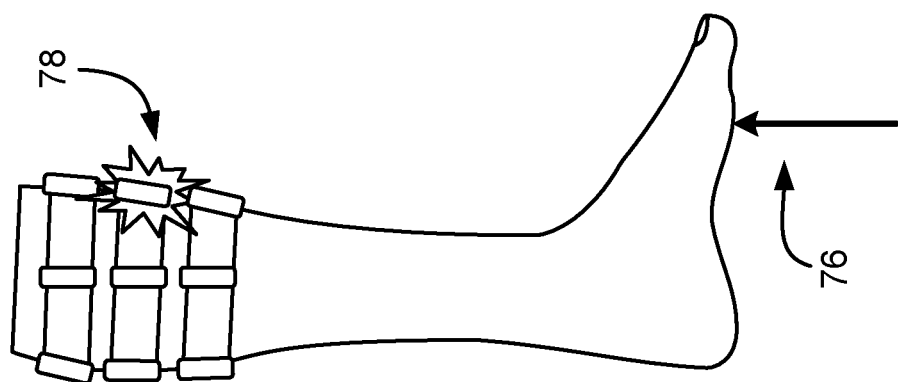
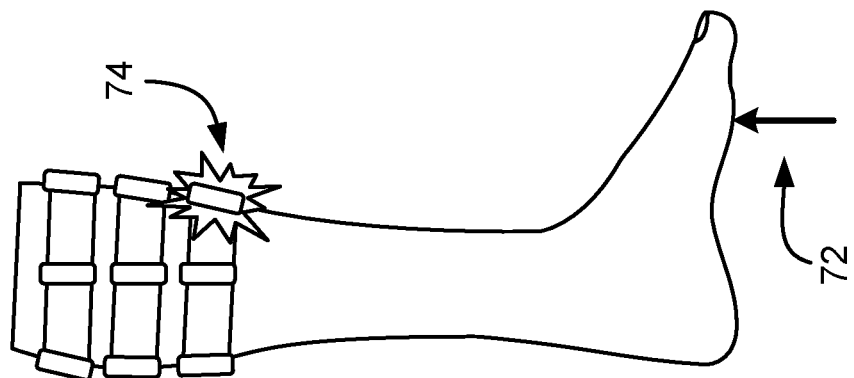
Fig. 7

FEEDBACK DEVICE FOR IMPROVED BALANCE CONTROL

CROSS-REFERENCE TO RELATED APPLICATION(S)

This application claims priority as a continuation of U.S. patent application Ser. No. 16/358,146, entitled "Feedback Device for Reduction of Foot Skin Damage in Patients with Sensory Loss" and filed Mar. 19, 2019; which claims priority as a continuation of U.S. patent application Ser. No. 16/119,558, entitled "Feedback Device for Reduction of Foot Skin Damage in Patients with Sensory Loss" and filed Aug. 31, 2018; which claims priority as a continuation of U.S. patent application Ser. No. 15/966,152, entitled "Prosthetic Limb Sensory System for Improved Balance Control" and filed Apr. 30, 2018; which claims priority as a continuation of U.S. Pat. No. 9,955,904, entitled "Sensory Prosthetic for Improved Balance Control," which issued May 1, 2018; which claims priority as a continuation of U.S. patent application Ser. No. 15/052,349, entitled "Sensory Prosthetic for Improved Balance Control" and filed Feb. 24, 2016; which claims priority as a continuation of U.S. Pat. No. 9,289,174, entitled "Sensory Prosthetic for Improved Balance Control," which issued on Mar. 22, 2016; which claims priority as a continuation of U.S. Pat. No. 9,402,580, entitled "Sensory Prosthetic for Improved Balance Control," which issued on Aug. 2, 2016, which claims priority as a continuation of U.S. Pat. No. 8,974,402, entitled "Sensory Prosthetic for Improved Balance Control," which issued on Mar. 10, 2015, which claims priority to U.S. Patent Application 60/372,148, entitled "Sensor Prosthetic for Improved Balance Control" and filed Apr. 12, 2002, all of which are hereby incorporated herein by reference in their entireties.

FIELD OF THE INVENTION

The present invention relates generally to systems for improving pressure control, and more specifically to a feedback device which measures pressure related information, and produces a stimulation that encodes that information.

BACKGROUND OF THE INVENTION

It has been estimated that as much as 20% of the elderly population in the United States may be suffering from peripheral neuropathies, largely as a consequence of diabetes. Peripheral neuropathic patients exhibit increased body sway during quiet standing. Peripheral neuropathies have been associated with increased thresholds for the perception of ankle inversion/eversion and a reduced ability to maintain a unipedal (single footed) stance, suggesting a reduction in balance control while walking. Epidemiological evidence has linked peripheral neuropathies with an increased risk of falling. Postural responses to floor perturbations in peripheral (diabetic) neuropathy patients are delayed and are poorly scaled to the perturbation amplitude The most common symptom of peripheral neuropathies is a reduction in sensation from the soles of the feet. A number of studies have provided evidence that afferent information from the feet is an important part of the balance control system. A recent study on adaptation to microgravity suggests that foot sole pressure may be critical for triggering the anticipatory postural adjustments that are normally required to maintain balance during arm movements.

For the above reasons and others, it would be desirable to have a sensory substitution system that effectively provides information regarding foot sole pressure distribution patients who are no longer able to acquire this information by natural means. The system should enable a patient wearing a device to achieve improved upright balance control, thereby reducing the patient's risk of falls and associated injuries. Such a system should further advantageously support integration of balance related feedback into the patient's unconscious postural control system, eventually eliminating the need for conscious effort in this regard.

BRIEF SUMMARY OF THE INVENTION

A feedback device is disclosed for measuring balance related information, and for producing a stimulation of the skin that encodes that information in a way that is useful to the wearer of the device. The disclosed device consists of at least one sensor for detecting balance information and for transmitting at least one balance information signal to a signal processing subsystem. The signal processing subsystem converts the received balance information signal into at least one stimulation control signal. The signal processing subsystem then transmits at least one stimulation control signal to at least one stimulator, which provides stimulation to a wearer of the device reflecting the stimulation control signal received from the signal processing subsystem.

In one embodiment, an array of sensors are arranged under the soles of each foot of the wearer. The sensors operate to transduce the magnitude of pressure exerted on the foot sole at each sensor location into a balance information signal. A signal processing subsystem operates to convert the balance information signals obtained from the sensors into estimates of the location and magnitude of the resultant ground reaction force exerted on each foot, generally referred to as center-of-pressure, or "COP". The signal processing subsystem then encodes the estimated COP into stimulation control signals that drive elements of a stimulator array. Further in such an embodiment, the stimulator is made up of an array of vibrotactile stimulators for placement on the user's leg in one or more planes (also referred to as on the user's leg in one or more planes (also referred to as vibrator "levels") approximately parallel to the plane of the foot sole. Stimulators are arranged within each plane corresponding to at least four locations on each leg: anterior, posterior, medial, & lateral. In response to signals produced by the signal processing subsystem, the stimulator array provides vibrotactile stimulation of the skin of the leg representing the estimated COP. In such an embodiment, the disclosed system provides a portable, wearable device, by which the subject receives cutaneous stimulation on the leg regarding the location and magnitude of the ground reaction force under the ipsilateral foot. With training, a patient suffering from reduced plantar sensation will learn to make postural corrections in response to this stimulation in the same manner as a healthy person would react to changes in the pressure distribution under their feet.

Thus there is disclosed a sensory substitution system for providing information regarding foot sole pressure distribution to users who are no longer able to acquire this information by natural means. A user wearing this device will achieve improved upright balance control, reducing their risk of falls and associated injuries. With practice, this encoded balance information provided by the device may be integrated into a patients unconscious postural control system, eliminating the need for conscious balancing effort. The disclosed system may also be embodied so as to reduce the balance deficits caused by prolonged exposure to reduced weight bearing, as seen in patients recovering from prolonged bed rest or in astronauts returning to terrestrial gravity. Preventative treatments with the disclosed device may also reduce the hypersensitivity of foot soles in some users, which would otherwise contribute to postural deficits.

BRIEF DESCRIPTION OF THE DRAWINGS

The invention will be more fully understood by reference to the following detailed description of the invention in conjunction with the drawings, of which:

FIG. 7 illustrates an example of force magnitude encoding in a multilevel stimulator embodiment.

DETAILED DESCRIPTION

All disclosures of provisional patent application Ser. No. 60/372,148 entitled "SENSORY PROSTHETIC FOR IMPROVED BALANCE CONTROL", and filed Apr. 12, 2002, are hereby incorporated by reference herein.

Figure 1:
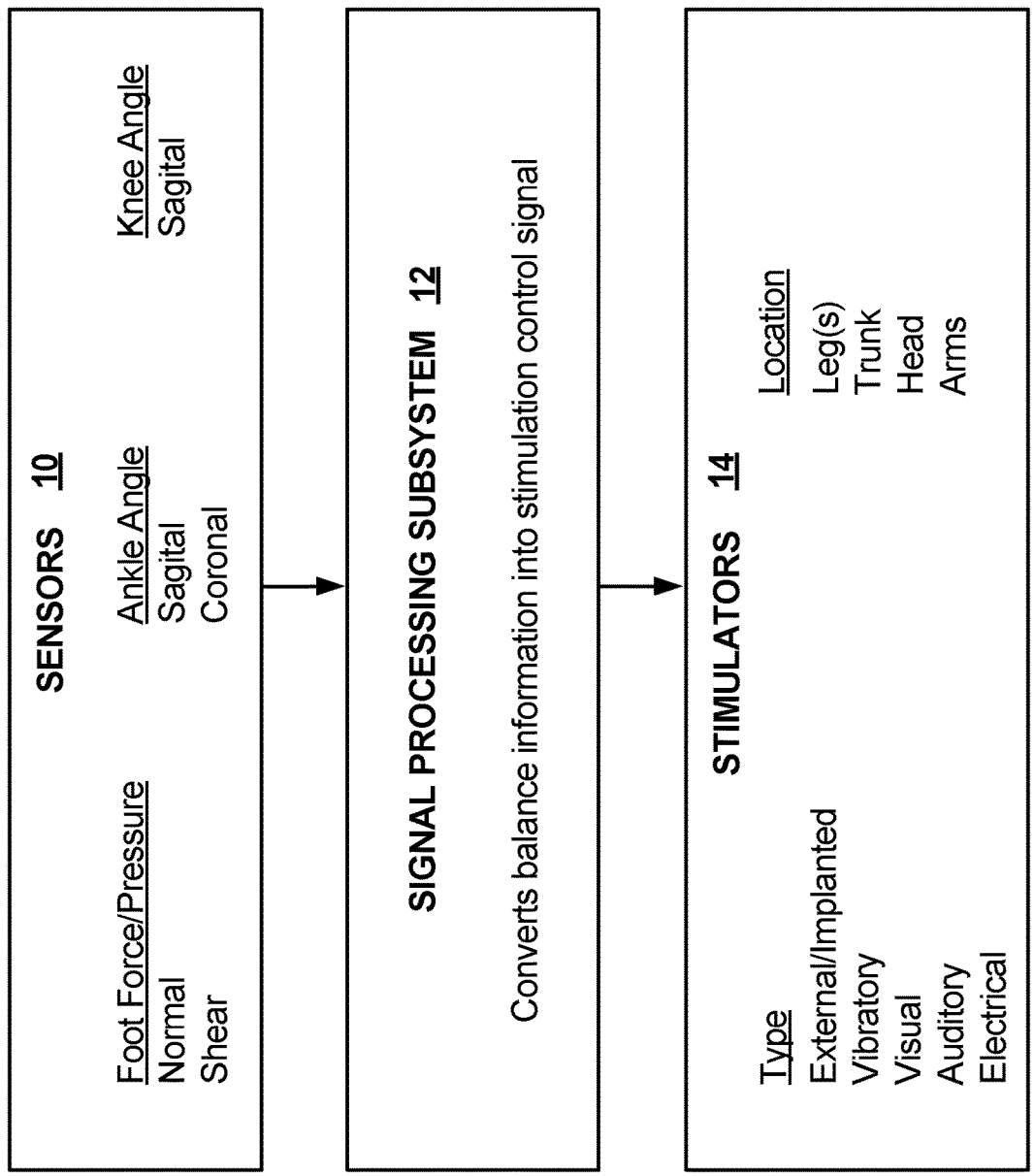
FIG. 1 shows the structure and operation of an illustrative embodiment of the disclosed system.

FIG. 1 shows the structure and operation of an illustrative embodiment of the disclosed system. As shown in FIG. 1, sensors 10 detect balance information that may represent foot force/pressure, such as normal and/or shear pressure, ankle angle, such as sagittal and/or coronal ankle angle, or knee angle, such as sagittal knee angle. The balance information detected by the sensors 10 is passed to a signal processing subsystem 12, which converts the balance information received from the sensors 10 into a stimulation control signal that is passed to the stimulators 14. The stimulators 14 operate in response to stimulation control signal, producing a stimuli to a user of the disclosed system representing the balance information detected by the sensors 10. The stimulators 14 may be of various types, including external and/or internal stimulators, and provide various types of stimuli, including vibratory, visual, auditory, and/or electrical stimuli. The stimulators 14 may be located on various parts of the body, including one or both legs, head, arms or trunk of the user.

Figure 2:
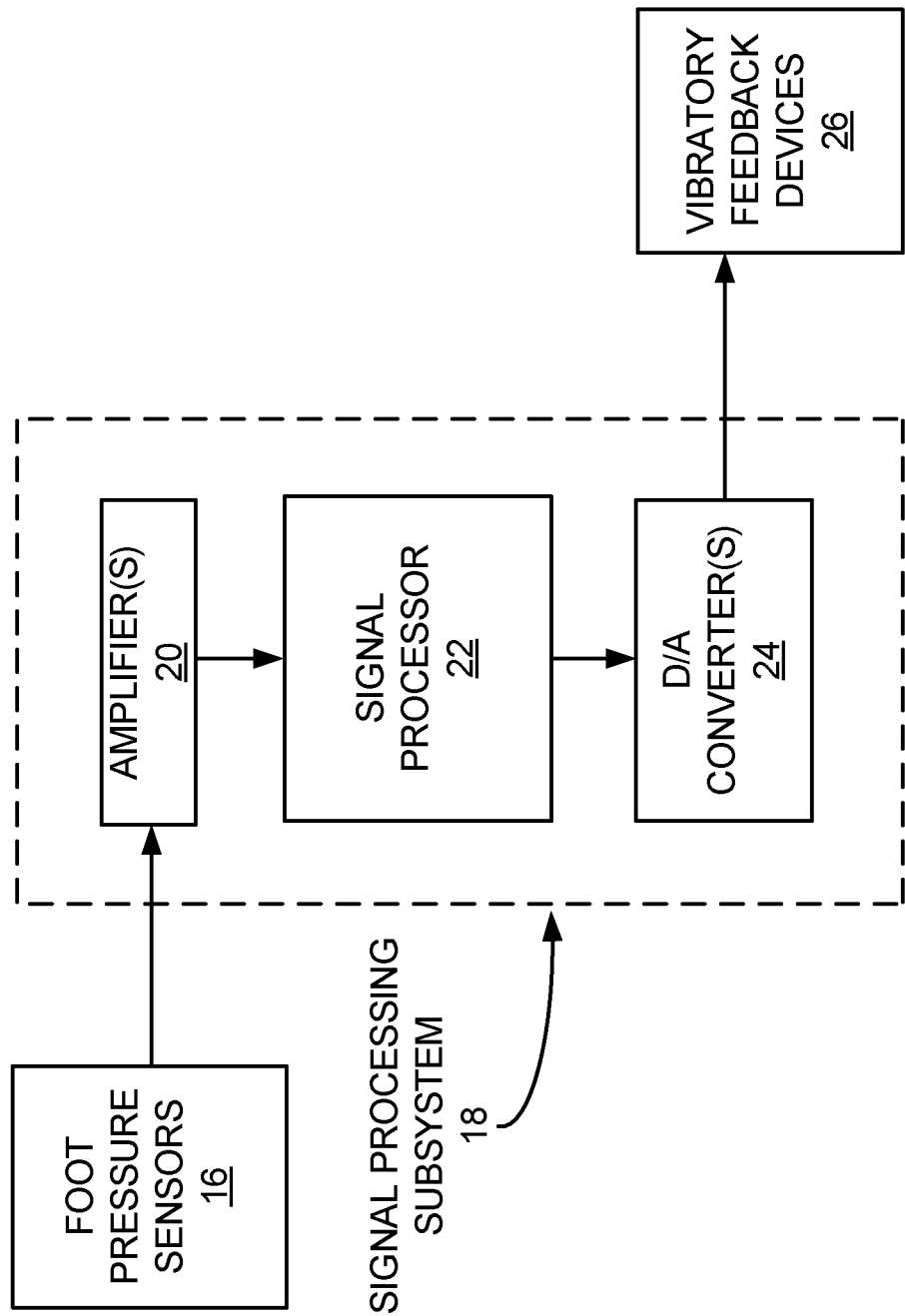
FIG. 2 shows a circuit diagram of a portion of an illustrative embodiment of the disclosed system.

FIG. 2 shows a circuit diagram of a portion of an illustrative embodiment of the disclosed system. As shown in FIG. 2, a number of foot pressure sensors 16 transmit at least one balance information signal to one or more amplifiers 20 within a signal processing subsystem 18. The amplifiers 20 may, for example, include one or more LM324 analog amplifiers supplied by National Semiconductor Corporation. The amplified signals output from the amplifiers 20 are passed to a signal processor 22. In the example of FIG. 2, the signal processor includes analog to digital processing functionality, as well as program code storage for code executable on the signal processor 22. The signal processor 22 may, for example, consist of a PIC 16F877 microcontroller, supplied by Microchip Technology, Inc. The signal processor 22 passes a digital stimulation control signal to one or more digital to analog converters 24, which convert the digital stimulation control signal to an analog stimulation control signal that is passed to one or more vibratory feedback devices 26. The vibratory feedback devices 26 provide a vibratory stimulus to a user wearing the vibratory feedback devices 26, such that the vibratory stimulus encodes and/or represents the balance information provided from the foot pressure sensors 16 to the signal processing subsystem 18. The digital to analog converters 24 may, for example, include one or more TLC7226IN, 8 bit, 4 channel digital to analog converters. The vibratory feedback devices may, for example, include one or more analog amplifiers, such as AD8534 analog amplifiers, supplied by Analog Devices, Inc., as well as a number of vibrators.

Figure 3:
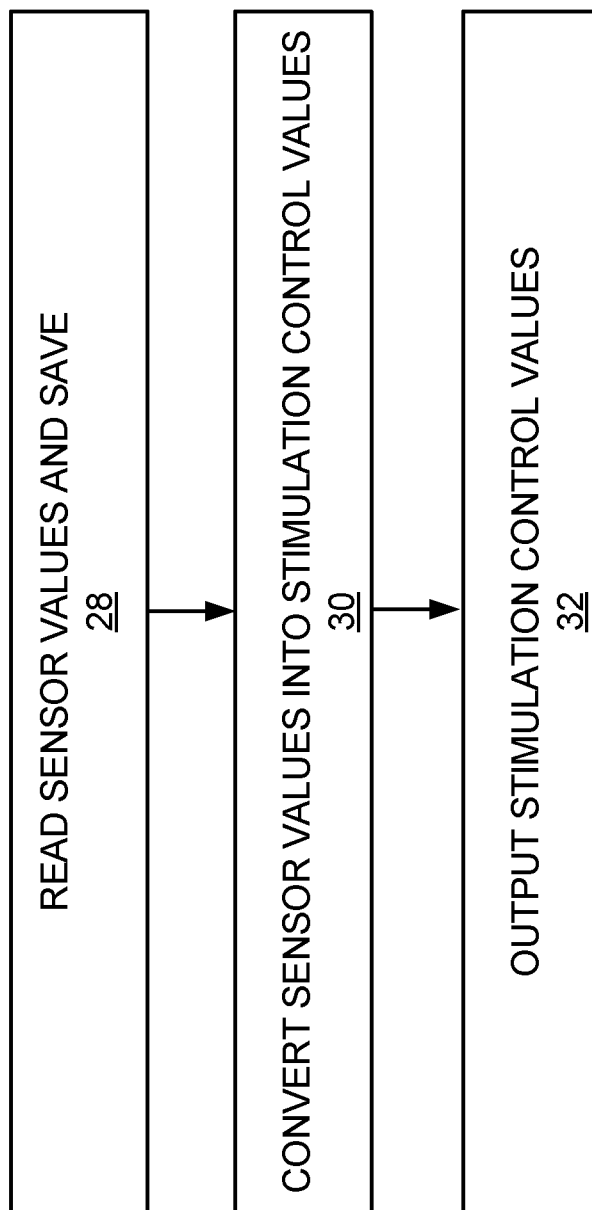
FIG. 3 is a flow chart showing steps performed during operation of an illustrative embodiment of the disclosed system.

FIG. 3 is a flow chart showing steps performed during operation of an illustrative embodiment of the disclosed system. The steps shown in FIG. 3 may, for example be performed at least in part by the signal processing subsystem 18 shown in FIG. 2, for example under control of an assembly language program stored within and executed on the signal processor 22 shown in FIG. 2. As shown in FIG. 3, at step 28, the disclosed system reads balance information signals output from one or more sensors, and stores, the values for subsequent processing. The disclosed system then operates to convert the stored sensor values into stimulation control values at step 30. The stimulation control values are then output at step 32.

An example of the processing performed by the signal processing subsystem to convert sensor values into stimulation control values is now provided. A formula describing the steps performed by the signal processing subsystem to convert sensor values into stimulation control values is as follows:

$$\Theta_l(t) = \sum_{n=1}^{N} f_{nl}(t)\theta_{nl}, \quad R_l(t) = \sum_{n=1}^{N} f_{nl}(t)r_{nl}, \quad (\text{Eq. 1})$$

$$F_l(t) = \frac{1}{W}\sum_{n=1}^{N} f_{nl}(t),$$

where $f_{nl}$=normal force, approximately perpendicular to the plane of the foot sole, measured by sensor array element n under leg 1, $\theta_{nl}$=angular position of sensor array element n under leg 1, $r_{nl}$=radial position of sensor array element n under leg 1, N=total number of sensor array elements under leg 1, W=total body weight of the wearer, $\Theta_l$=angular position of center-of-pressure under leg 1, $R_l$=radial position of center-of-pressure under leg 1, $F_l$=portion of body weight supported by leg 1, and, t=a variable representing discrete time $$Q_{\Theta l}(t) = P_\Theta \Theta_l(t) + D_\Theta \frac{d\Theta_l(t)}{dt} + \quad (\text{Eq. 2})$$

$$I_\Theta \sum_{x=t-u_\Theta}^{t} \Theta_l(z) + P_\beta \beta_l(t) + D_\beta \frac{d\beta_l(t)}{dt} + I_\beta \sum_{x=t-u_\beta}^{t} \beta_l(z),$$

-continued $$Q_{Rl}(t) = \quad \text{(Eq. 3)}$$
$$P_R R_l(t) + D_R \frac{dR_l(t)}{dt} + I_R \sum_{x=t-u_R}^{t} R_l(z) + P_\lambda \lambda_l(t) + D_\lambda \frac{d\lambda_l(t)}{dt} +$$
$$I_\lambda \sum_{x=t-u_\lambda}^{t} \lambda_l(z) + P_\alpha \alpha_l(t) + D_\alpha \frac{d\alpha_l(t)}{dt} + I_\alpha \sum_{x=t-u_\alpha}^{t} \alpha_l(z),$$

$$Q_{Fl}(t) = P_F F_l(t) + D_F \frac{dF_l(t)}{dt} + I_F \sum_{z=t-u_F}^{t} F_l(z), \quad \text{(Eq. 4)}$$

where $\beta_l$=the magnitude of the angle existing between the approximate longitudinal axis of foot 1 and the projection of the approximate longitudinal axis of the ipsilateral shank onto a plane substantially parallel to the sole of foot 1, $\lambda_l$=the magnitude of the angle existing between the approximate longitudinal axis of shank 1 and a plane substantially parallel to the sole of foot 1, $\alpha_l$=the magnitude of the angle existing between a line substantially parallel to the longitudinal axis of shank 1 and a line substantially parallel to the longitudinal axis of the ipsilateral femur, z=a variable representing discrete time, d/dt=the operator indicating a discrete-time estimation of the first derivative, Σ=the summation operator, $P_\theta$, $D_\theta$, $u_\theta$, $P_\beta$, $D_\beta$, $I_\beta$, $u_\beta$, $P_R$, $D_R$, $I_R$, $u_R$, $P_\lambda$, $D_\lambda$, $I_\lambda$, $u_\lambda$, $P_\alpha$, $I_\alpha$, $u_\alpha$, $P_F$, $D_F$, $I_F$, $u_F$ are time-invariant coefficients.

An example of an algorithm for the processing performed by software or firmware stored in and executed by a microcontroller in the signal processing subsystem is as follows:

Algorithm:

```
for v = 1 to V
    for p = 1 to P
        if {(A_V ≤ Q^J1(t) < A_{V+1}) ∩ (B_{p-} ≤ Q_{θ1}(t) ≤ B_{p+})} = true,
            then S_{[v,p]1} (t) = h(Q_{K1} (t), Q_{θ1} (t))
        else S_{[v,p]1} (t) = 0
    end
end
``` where subscripts J and K correspond to subscripts F and R in Equations 3 & 4: (J=F and K=R) or (J=R and K=F),

[v,p] denotes the spatial coordinates of an individual stimulator within the stimulation array, v being an integer denoting the vertical index and p being an integer denoting the horizontal index of the stimulator at location [v,p], ∩ n denotes the logical AND operation, V=total number of horizontal rows in the stimulation array, P=total number of vertical columns in the stimulation array, $A_j$=the threshold of $Q_{J1}(t)$ for activation of a stimulator in the jth row of the stimulator array, $B_{j-}$=the minimum value of $Q_{\theta1}(t)$ for activation of a stimulator in the jth column of the stimulator array, $B_{j+}$=the maximum value of $Q_{\theta1}(t)$ for activation of a stimulator in the jth column of the stimulator array, $h(Q_{K1}(t), Q_{\theta1}(t))$ is a piecewise-continuous function of $Q_{K1}(t)$ and $Q_{\theta1}(t)$, and $S_{[v,p]1}$ is the magnitude of activation of stimulator [v,p] within the stimulator array attached to leg 1. $S_{[v,p]1}$ may denote the amplitude or frequency of stimulation produced by stimulator [v,p].

In a preferred embodiment, with regard to the stimulators, 3 vibrator rows are used to encode load, 4 vibrator columns are used to encode polar center-of-pressure (COP) orientation, and vibrator activation voltage (proportional to frequency) is used to encode polar radius of COP. Vibrator frequency is normalized over its active range to an elliptical ring with ranges of 1 to 8 mm in the mediolateral direction and 2 to 20 mm in the anteroposterior direction. These ranges were selected based upon the typical range of human movement during quiet stance and would be increased in order to optimize the device for dynamic activities such as walking. The position of force transducers under the foot soles corresponds to a foot corresponding to a U.S. Men's size 9 shoe. Illustrative parameter values for an example of the preferred embodiment are therefore provided for purposes of explanation as follows:

N=7, $r_1$=75, $r_2$=80, $r_3$=90, $r_4$=120, $r_5$=70, $r_6$=80, $r_7$=115, (units in mm)

$\theta_1$=0.70, $\theta_2$=1.05, $\theta_3$=1.39, $\theta_4$=1.74, $\theta_5$=2.09, $\theta_6$=4.36, $\theta_7$=4.89, (units in radians)

V=3, P=4,

J≡F, K≡R, $P_\theta=P_R=P_F=1$; $P_\beta=P_\lambda=P_\alpha=0$; $D_\theta=D_R=D_F=D_\beta=D_\lambda=D_\alpha=0$, $I_\theta=I_R=I_F=I_\beta=I_\lambda=I_\alpha=0$, $A_1$=0.25 W, $A_2$=0.5 W, $A_3$=0.75 W, $B_{1-}$=−0.25π rad, $B_{1+}$=0.25π rad, $B_{2-}$=0.25π rad, $B_{2+}$=0.75π rad, $B_{3-}$=0.75π rad, $B_{3+}$=1.25π rad, $B_{4-}$=1.25π rad, $B_{4+}$=1.75π rad $$h \equiv (Q_{Rl}(t) - R_o) \frac{V_{max} - V_{min}}{17} \text{ for } Q_{Rl}(t) > R_o$$

$$h \equiv 0 \text{ for } Q_{Rl}(t) \leq R_o$$

where $$R_o = \sqrt{\frac{1}{\cos^2 Q_{\theta l}(t) + \frac{\sin^2 Q_{\theta l}(t)}{9}}}$$

$V_{max}$ = 5 volts and $V_{min}$ = 2.5 Volts

In an alternative embodiment, Equation 1 above also includes calculation of the total shear force impinging on the sole of foot 1, and Equation 2 and/or 3 includes terms pertaining to the total shear force, the derivative of the total shear force, and the integral summation of the total shear force impinging on foot 1. Thus the representation of balance information by the stimulator array reflects information regarding the shear forces impinging on the soles of the user's feet.

Neuropathic patients often encounter sustained elevated pressures under parts of their feet that result in skin damage and the development of an ulcer. Consistent with the algorithm above, the disclosed system may operate such that signal processing subsystem transmits signals to the stimulators reflecting the time histories of pressures or forces impinging on individual transducers within a sensor array. The resulting stimulation to a wearer of such an embodiment indicates when and where the forces or pressures impinging on an individual transducer within the sensor array have exceeded a predetermined instantaneous or time integral threshold.

While in the above algorithm the terms foot, shank and femur are used to describe body parts of a wearer of an embodiment of the disclosed system, those skilled in the art will recognize that other terms may be used in the alternative to describe the same parts. For example, alternative, corresponding terms to those used in the algorithm above include lower leg for shank, and upper leg for femur.

Figure 4:
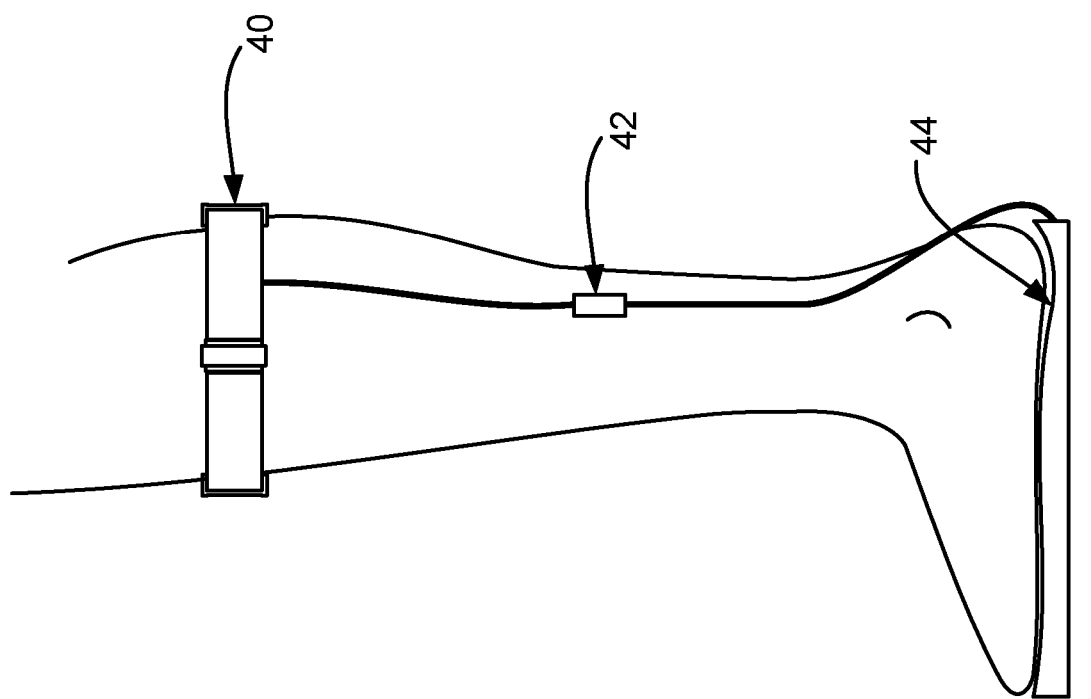
FIG. 4 shows an illustrative embodiment of the disclosed system using a single level stimulation array.

FIG. 4 shows an illustrative embodiment of the disclosed system using a single level stimulation array 40. As shown in FIG. 4, the illustrative embodiment includes a vibrotactile feedback array 40, a microprocessor controller subsystem 42, and a foot sole pressure sensor array 44. In the illustrative embodiment of FIG. 4, vibrotactile or electrotactile cutaneous feedback provided through the stimulation array 40 encodes position of foot Center-Of-Pressure and/or weight distribution by modulating one or more of the following: stimulus frequency, stimulus amplitude, location of stimulus or number of active stimulators. This stimulation array 40 is located adjacent to the skin of the leg or thigh. The location of active stimulator(s) on the skin in the transverse plane directly reflects the location of the foot Center-of-Pressure in the transverse plane.

The microprocessor controller subsystem 42 operates to convert electrical or mechanical signal(s) from the sensor array 44 into signal(s) which control the activity of elements within the feedback array 40. The microprocessor controller subsystem 42 may be implemented as a discrete system component or be imbedded within the other components. The microprocessor controller subsystem 42 estimates the position of the Center-of-Pressure {COP} under the foot and/or the fraction of the body weight supported by the foot. These estimates are then used to produce an appropriate output signal to the feedback array 40. A "dead-zone" may be implemented such that Center-of-Pressure position within a certain range and/or foot load below a certain threshold may produce no output to the feedback elements.

Figure 5:
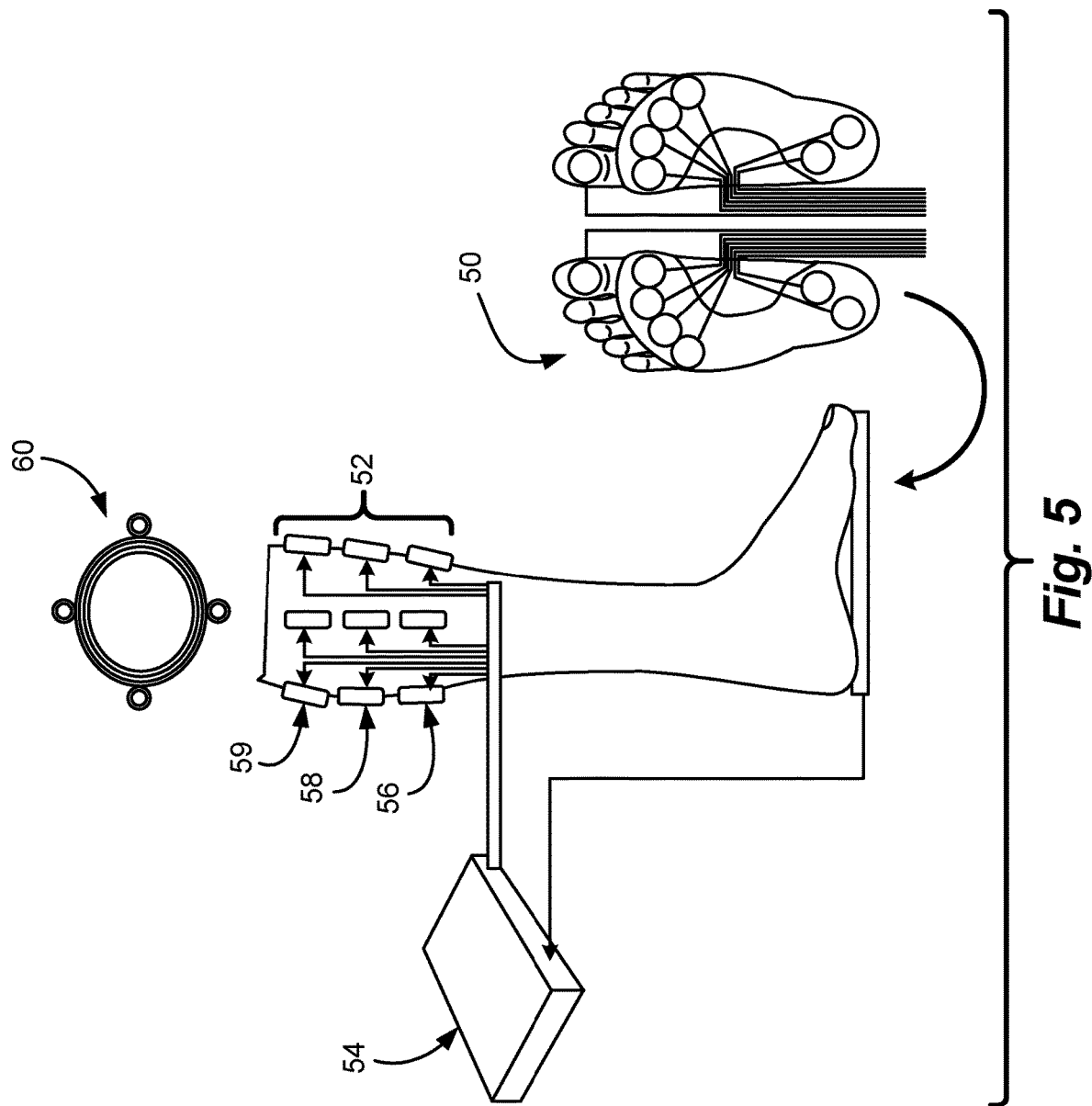
FIG. 5 shows an illustrative embodiment of the disclosed system using a multi-level stimulation array.

FIG. 5 shows an illustrative embodiment of the disclosed system using a multi-level stimulation array. The illustrative embodiment of FIG. 5 includes an array of force sensing resistors {FSRs} 50 placeable under the soles of one or more feet of a user. Balance information from the array of force sensing resistors 50 is passed to a microprocessor data acquisition and processing subsystem 54. The subsystem 54 operates to convert the balance information it receives into stimulation control signals sent to a vibro-tactile array 52 located on one or more legs of the user. The vibro-tactile array 52 includes three vibrator levels 56, 58, and 59. A top view 60 of the vibrotactile array on the leg or legs of the user illustrates that each of the levels 56, 58 and 59 include four vibrators located in the front, back, and both sides of the leg or legs.

Figure 6:
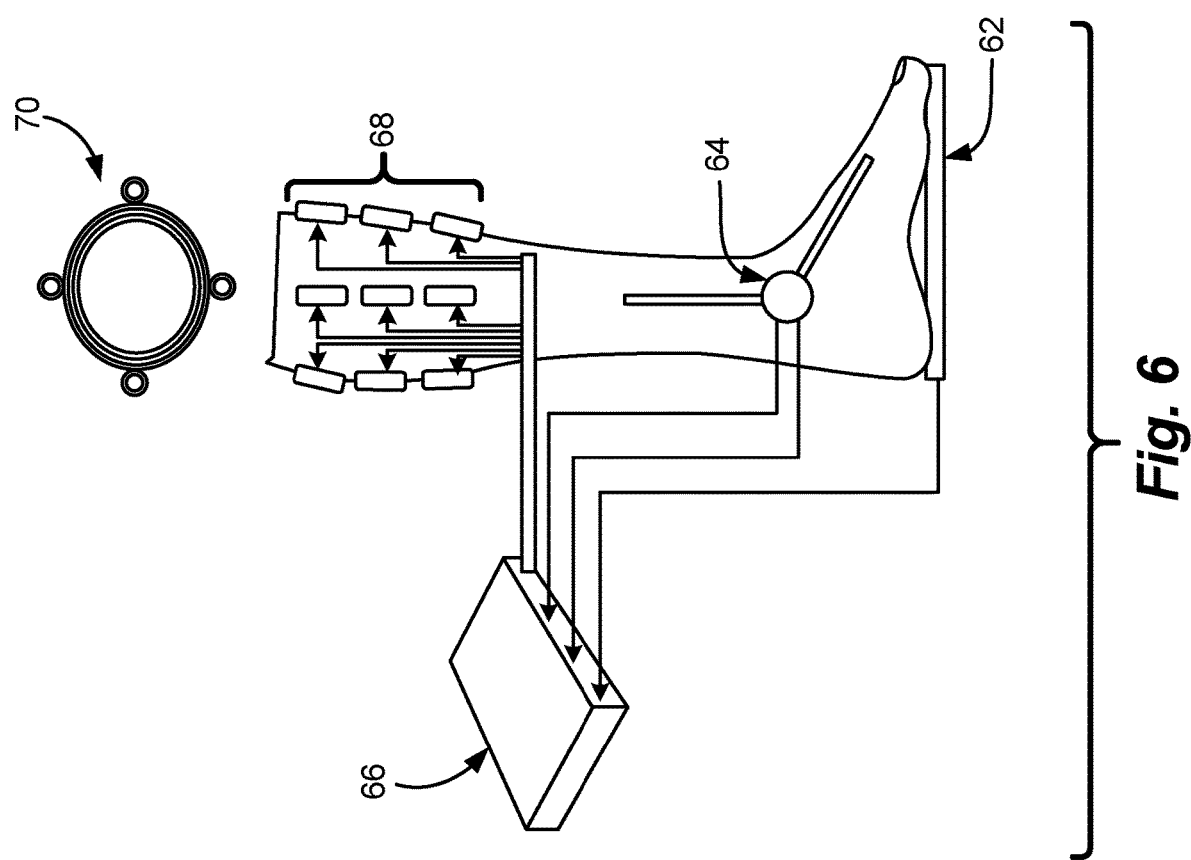
FIG. 6 shows an illustrative embodiment of the disclosed system using a multi-level stimulation array in combination with a bi-axial goniometer.

FIG. 6 shows an illustrative embodiment of the disclosed system using a multi-level stimulation array in combination with a bi-axial goniometer. As shown in FIG. 6, a force pressure sensor array 62 and a bi-axial goniometer 64 operate to provide balance information to a microprocessor data acquisition and processing subsystem 66. The bi-axial goniometer 64 provides information regarding detected ankle angle with regard to the angle of the user's foot to the corresponding lower leg. The stimulation array 68 on the user leg is shown as a multilevel vibrator array, and the top view 70 of the stimulation array 68 illustrates that each level of vibrators in the stimulation array 68 includes four vibrators, mounted in the front, back, and both sides of the leg.

FIG. 7 illustrates an example of force magnitude encoding in a multilevel stimulator embodiment. FIG. 7 illustrates that a first, relatively low level force 72, may be encoded as a vibrational stimulus 74 on a lowest vibrator layer (or level) of the stimulation array. Similarly, a relatively high level force 80, may be encoded as a vibrational stimulus 82 on a highest vibrator layer (or level) of the stimulation array. Along these same lines, a force 76 between the forces 72 and 80 may be encoded as a vibrational stimulus 78 within a middle vibrator layer of the stimulation array. Thus FIG. 7 shows how a magnitude represented in the balance information signal, such as a ground reaction magnitude, can be communicated to the user through levels within a stimulator array attached or proximate to the user.

Figure 8:
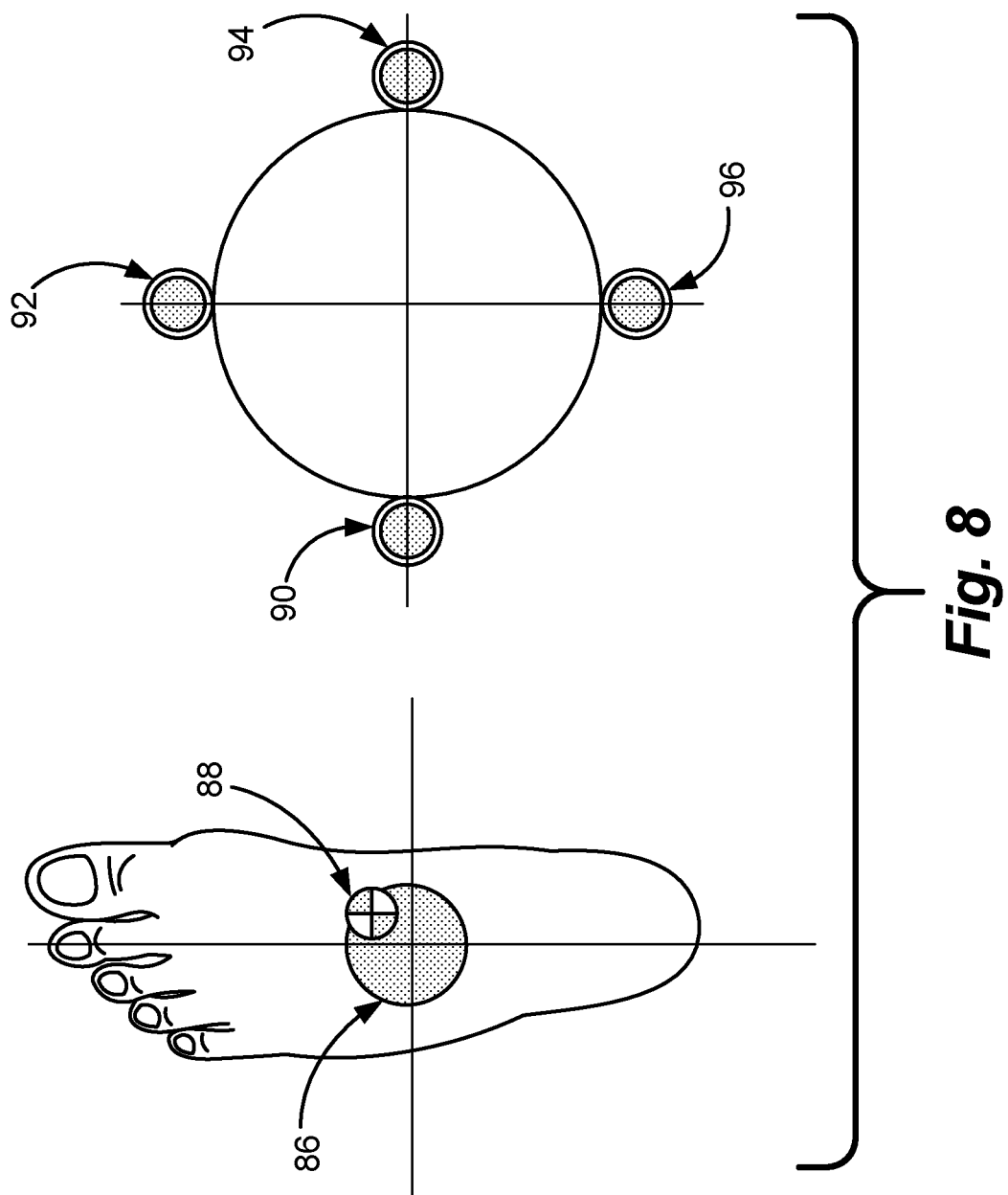
FIG. 8-12 show the mapping of balance information to stimulation points in an illustrative embodiment.

FIGS. 8-12 show the mapping of balance information to stimulation points in an illustrative embodiment, and thus illustrate mapping of COP information onto a body part, in this case, a leg of the user. FIG. 8 shows a "dead zone" 86, representing a predetermined physical area under a user's foot. In an illustrative embodiment of the disclosed system, if a center of pressure is estimated to be located within the dead zone, no stimulus is provided to the user. In such a case, the user is significantly balanced on the foot in question. As shown in FIG. 8, in the event that a center of pressure 88 is determined to be within the predetermined dead zone, no vibrational stimulus is provided in any of the vibrators 90, 92, 94 or 96, shown within a single level of stimulators mounted on a user's leg in a plane parallel to an array of sensors mounted under the user's foot or feet.

Figure 9:
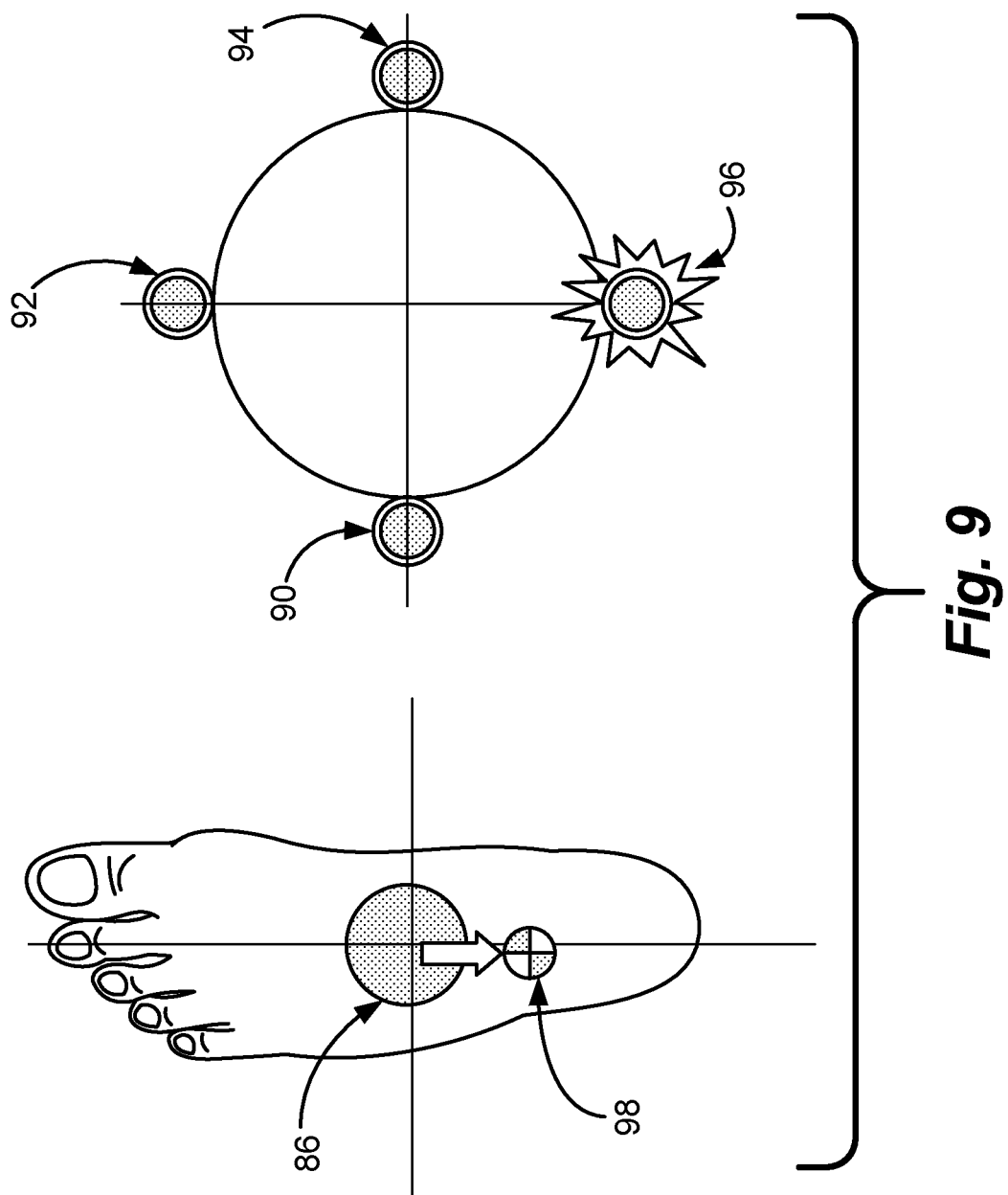

FIG. 9 illustrates operation of an embodiment of the disclosed system in the event that a center of pressure 98 is estimated to be located towards the back of the user's foot. Under such circumstances, a vibrator 96 located towards the back of the user's leg is shown providing a vibrational stimulus to the user.

Figure 10:
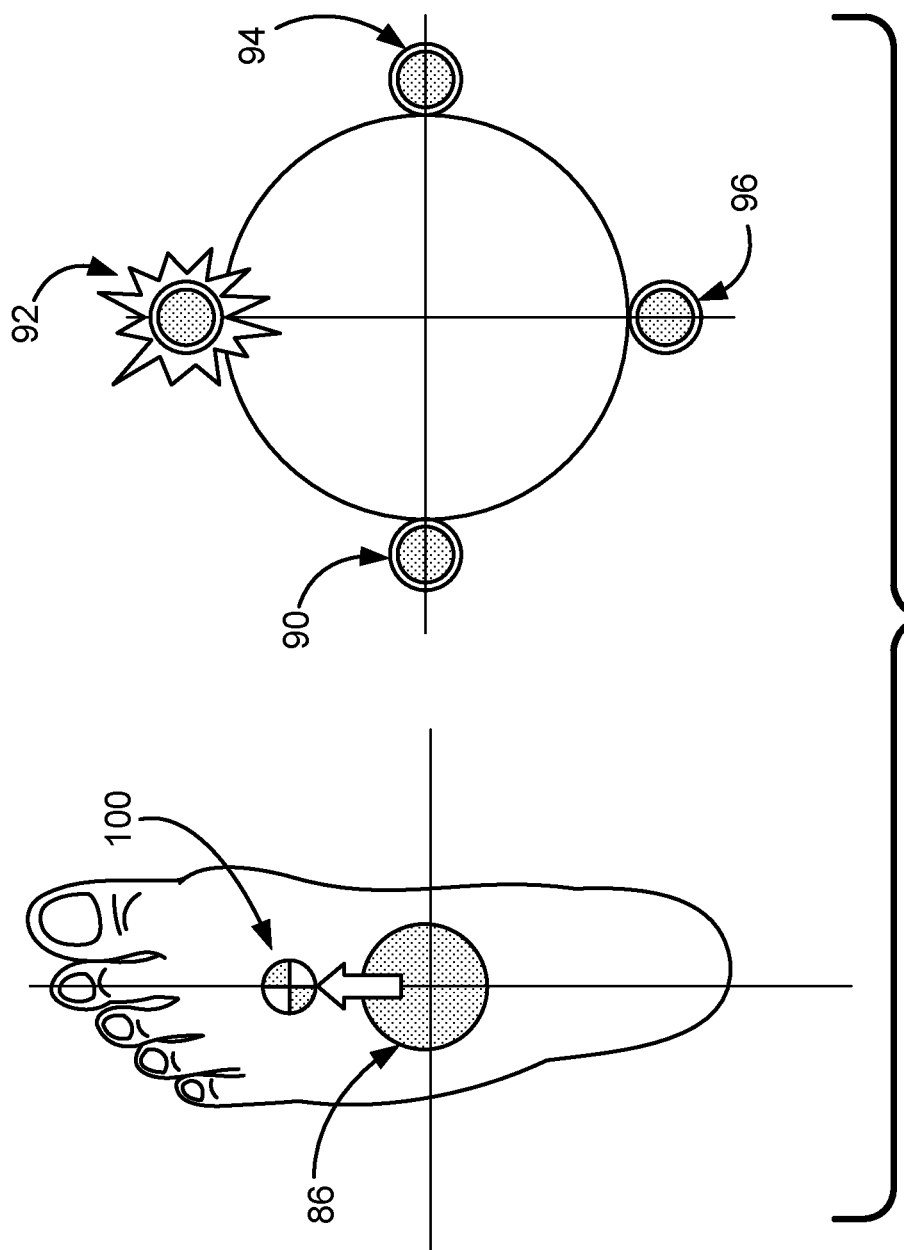

FIG. 10 illustrates operation of an embodiment of the disclosed system in the event that a center of pressure 100 is estimated to be located towards the front of a user's foot. Under such circumstances, a vibrator 92 located towards the front of the user's leis shown providing a vibrational stimulus to the user.

Figure 11:
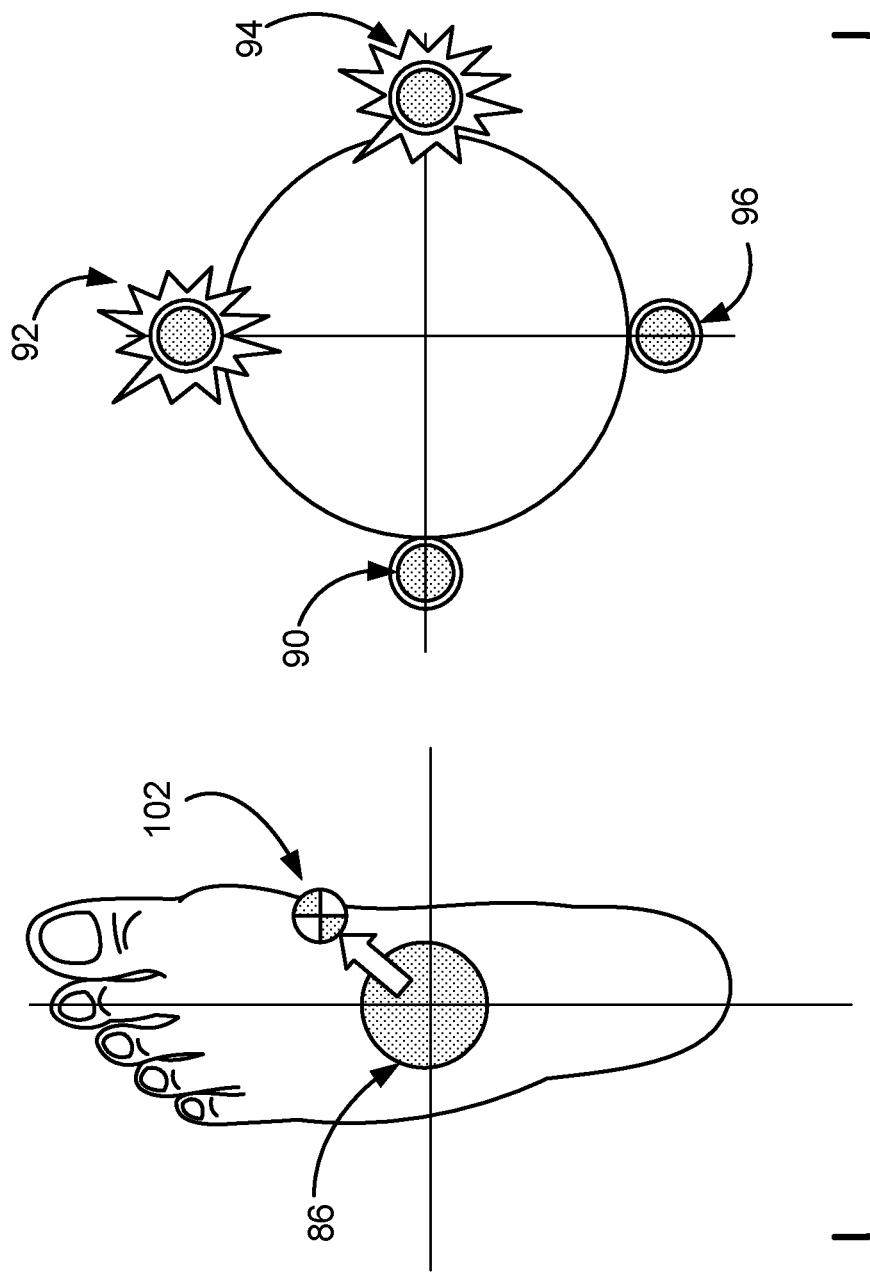

FIG. 11 illustrates operation of an embodiment of the disclosed system in the event that a center of pressure 102 is estimated to be located towards the front and right side of the user's foot. Under such circumstances, a vibrator 92 located towards the front of the user's leg, and a vibrator 94 located towards the right of the user's leg are shown providing a vibrational stimulus to the user.

Figure 12:
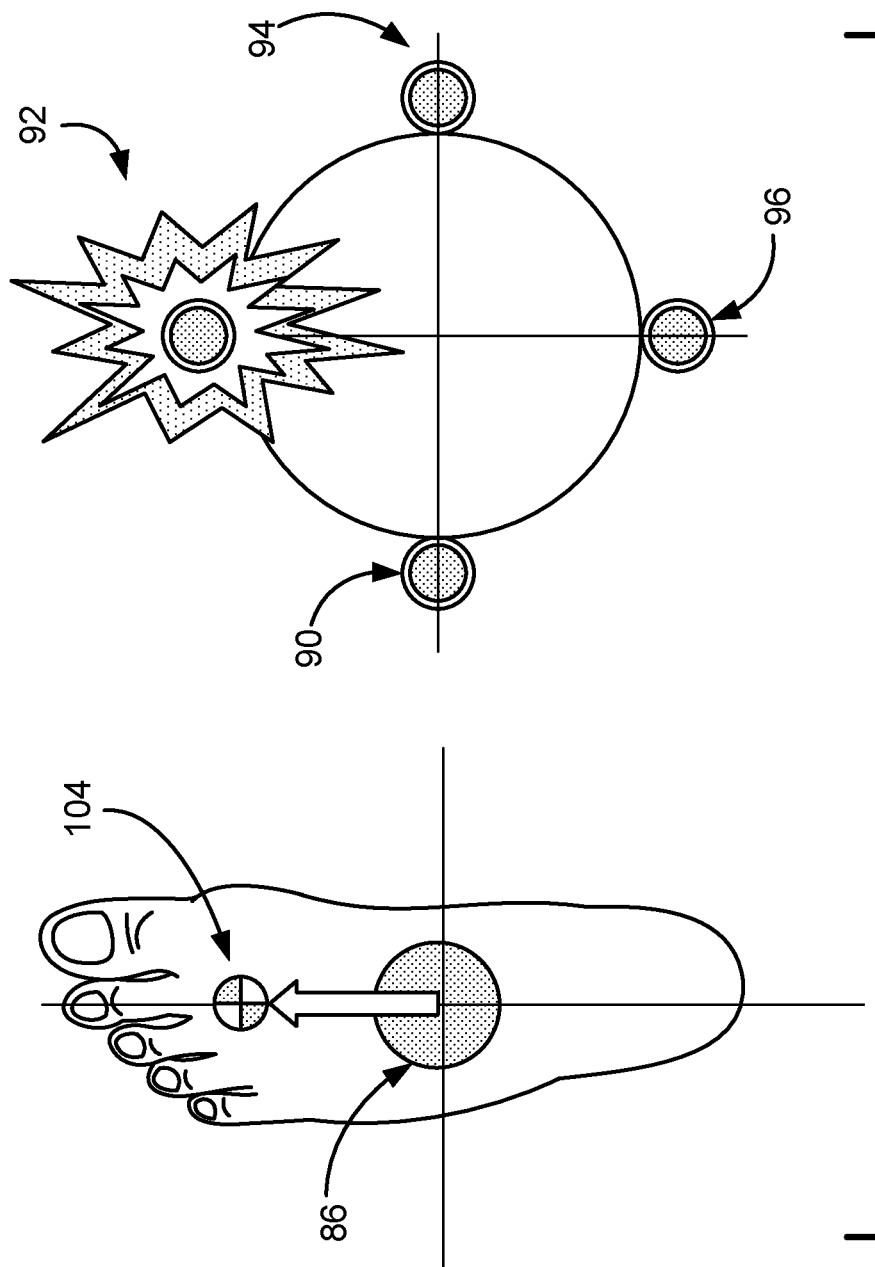

FIG. 12 illustrates frequency encoded magnitude stimulus in an illustrative embodiment. In the embodiment illustrated by FIG. 12, a relative increase in vibration frequency in one or more vibrators within the stimulation array is triggered by an increase in the polar radial distance of the center of pressure from a coordinate frame located near the center of the foot, or from the edge of the dead zone.

As shown in FIG. 12, the radial distance of the center of pressure from the center of the user's foot may be encoded using the frequency of vibration caused to occur in one or more vibrators in the stimulation array. As shown in FIG. 12, an estimated center of pressure 104, located towards the front of the user's foot, and being relatively farther from the center of the user's foot, may be represented to the user by causing the vibrator 92 in the stimulation array to vibrate at a relatively higher frequency. Such a higher frequency vibration thus represents the further distance of the estimated center of pressure from the center of the foot to the user. For example, the distance of the estimated center of pressure 104 from the center of the foot in FIG. 12 is greater than the distance of the estimated center of pressure 102 from the center of the foot in FIG. 11. Accordingly, the frequency of vibration of the vibrator 92 in FIG. 12 is greater than the frequency of vibration of the vibrators 92 and 94 in FIG. 11.

The disclosed system provides many and various advantages over previous systems. Specifically, the simplification of the balance information feedback provided by the disclosed system can more easily be integrated into the user's unconscious postural control system. The reduction of individual pressure signals by the disclosed system into an estimate of COP position and magnitude under each foot is easier to integrate into the postural control system than information regarding a number of separate pressure transducers.

A further advantage of the disclosed system relates to the coding of balance information using frequency modulation in addition to or as an alternative to amplitude modulation. Cutaneous stimulation has been shown to excite cutaneous mechanoreceptors on a 1 to 1 basis for a wide range of input frequencies. As a result, some cutaneous mechanoreceptors will respond to an artificial stimulation (vibrotactile or electrotactile) in the same manner as they would respond to a pressure stimulus. Simulating a natural pressure stimulus with an artificial one in this manner should facilitate the integration of this information into the unconscious balance control system.

Moreover, the location of feedback stimulators on the legs and oriented in a plane parallel to the plane of the foot sole should facilitate the integration of feedback information into the unconscious balance control system.

A number of specific variations and modifications are foreseen within the scope of the present invention. The following are some examples of variations and modifications:

1. The sensor array and/or stimulation array may be incorporated into a stocking, shoe, or boot.
2. The sensors may be embodied to acquire, encode, and provides feedback regarding shear forces under the user's foot or feet.
3. The sensors may be embodied to acquire, encode, and provide balance information regarding angle and or angular velocity of the lower leg with respect to the foot.
4. The disclosed system may be embodied to stimulate the cutaneous foot sole for the purpose of reducing postural deficits associated with long-term exposure to reduced foot loads, such as those incurred by bedridden patients on earth or astronauts in microgravity.
5. The disclosed system may be embodied to stimulate the cutaneous foot sole for the purpose of producing an artificial feeling of pressure or shear force, such as might be used in virtual environments.
6. The disclosed system may be embodied to stimulate the skin of a part of the body other than the foot sole for the purpose of producing an artificial feeling of pressure or shear force, such as might be used in virtual environments.
7. The disclosed system may be embodied to stimulate the cutaneous foot sole in response to pressure under the foot for the purpose of amplifying the sensation of pressure.
8. The disclosed system may be embodied to implement a signal processing method such that a range of COP positions and/or magnitudes produce no output from the feedback array (i.e. sensory "dead zone").
9. The mode of feedback may be embodied as tactile, vibrotactile, electrotactile, visual, thermal, and/or auditory.
10. The sensor array is implanted into or under the skin or within the body.
11. The feedback array may be implanted into or under the skin or within the body.
12. The stimulation array may be implanted such that the feedback elements are adjacent to or in contact with one or more sensory neurons or sensory nerves.
13. The sensor array may be affixed to or embedded within a prosthetic limb.
14. The communication between any or all of the device components may be wireless.
15. The sensor signals and/or feedback signals may be monitored remotely or recorded for the purpose of evaluating the effect or function of the device.

Those skilled in the art should appreciate that while the illustrative embodiments may implement the functions of the signal processing subsystem in computer software, these functions may alternatively be embodied in part or in whole using hardware components such as Application Specific Integrated Circuits, Field Programmable Gate Arrays, or other hardware, or in some combination of hardware components and software components.

While the invention is described through the above exemplary embodiments, it will be understood by those of ordinary skill in the art that modification to and variation of the illustrated embodiments may be made without departing from the inventive concepts herein disclosed. Accordingly, the invention should not be viewed as limited except by the scope and spirit of the appended claims.

What is claimed is:

1. A system for assisting the maintenance of balance of a user, the system comprising:
   a) at least one sensor positionable against or adjacent to a body part of the user, wherein the at least one sensor is configured to generate, during user stance and dynamic activities, user balance information signals and transmit the user balance information signals;
   b) a signal processing subsystem, the subsystem configured to receive the user balance information signals, and generate, based on the user balance information signals, balance control signals reflecting user balance information; and
   c) at least one stimulator configured to be positionable against or adjacent to a skin area of the user, the at least one stimulator configured to be responsive to the balance control signals to provide skin stimulation during the user stance and dynamic activities to the skin area of the user, thereby providing feedback to the user.

2. The system of claim 1, wherein the at least one sensor is configured to sense an ankle angle, a knee angle, or force.

3. The system of claim 1, wherein the user balance information comprises an amount of force.

4. The system of claim 1, wherein the body part comprises a foot, wherein the at least one sensor is positionable beneath the foot.

5. The system of claim 4, wherein the skin area is on the foot, wherein the at least one stimulator is positionable beneath the foot.

6. The system of claim 1, wherein the at least one stimulator is a vibrational stimulator.

7. The system of claim 1, wherein the at least one stimulator comprises an electrical, electrocutaneous, visual, auditory, or thermal stimulator.

8. The system of claim 1, wherein the at least one stimulator is positionable proximate to one or more sensory nerves of the user.

9. The system of claim 1, wherein the skin area is on a leg of the user.

10. The system of claim 1, wherein the skin area is on a sole of a foot, the trunk, the head, an arm, or a leg of the user.

11. A system for assisting the maintenance of balance of a user, the system comprising:
   a) at least one sensor positionable against a limb of the user, wherein the at least one sensor is configured to generate, during user stance and dynamic activities, user balance information signals and transmit the user balance information signals;
   b) a signal processing subsystem, the subsystem configured to receive the user balance information signals, and generate, based on the user balance information signals, balance control signals reflecting user balance information; and
   c) at least one stimulator configured to be positionable in contact with a skin area of the user, the at least one stimulator configured to be responsive to the balance control signals to provide skin stimulation during the user stance and dynamic activities to the skin area of the user, thereby providing feedback to the user.

12. The system of claim 11, wherein the at least one sensor is configured to sense an ankle angle, a knee angle, or force.

13. The system of claim 11, wherein
   the user balance information comprises an amount of force,
   the limb comprises a foot, wherein the at least one sensor is positionable beneath the foot, and
   the skin area is on the foot, wherein the at least one stimulator is positionable beneath the foot.

14. The system of claim 11, wherein the at least one stimulator is a vibrational stimulator.

15. The system of claim 11, wherein the at least one stimulator comprises an electrical, electrocutaneous, visual, auditory, or thermal stimulator.

16. The system of claim 11, wherein the at least one stimulator is positionable proximate to one or more sensory nerves of the user.

17. The system of claim 11, wherein the skin area is on a leg of the user.

18. The system of claim 11, wherein the skin area is on a sole of a foot, the trunk, the head, an arm, or a leg of the user.

19. A method for assisting the maintenance of balance of a user, the method comprising:
   sensing, with at least one sensor, user balance information,
   generating, during user stance and dynamic activities, user balance information signals based on the user balance information;
   transmitting the user balance information signals to a signal processing subsystem;
   generating, based on the user balance information signals, balance control signals reflecting the user balance information; and
   stimulating a skin area of the user with at least one stimulator during the user stance and dynamic activities based on the balance control signals, thereby providing feedback to the user.

20. The method of claim 19, wherein the at least one stimulator is a vibrational stimulator.

* * * * *

UNITED STATES PATENT AND TRADEMARK OFFICE
CERTIFICATE OF CORRECTION

PATENT NO. : 10,653,352 B2
APPLICATION NO. : 16/522195
DATED : May 19, 2020
INVENTOR(S) : Oddsson et al.

Page 1 of 1

It is certified that error appears in the above-identified patent and that said Letters Patent is hereby corrected as shown below:

In the Specification

At Column 1 delete Lines 7-35 and insert:
--This application claims priority as a continuation of U.S. Patent Application 16/358,146, entitled "Feedback Device for Reduction of Foot Skin Damage in Patients with Sensory Loss" and filed March 19, 2019; which claims priority as a continuation of U.S. Patent Application 16/119,558, entitled "Feedback Device for Reduction of Foot Skin Damage in Patients with Sensory Loss" and filed August 31, 2018; which claims priority as a continuation of U.S. Patent Application 15/966,152, entitled "Prosthetic Limb Sensory System for Improved Balance Control" and filed April 30, 2018; which claims priority as a continuation of U.S. Patent 9,955,904, entitled "Sensory Prosthetic for Improved Balance Control," which issued May 1, 2018; which claims priority as a continuation of U.S. Patent Application 15/052,349, entitled "Sensory Prosthetic for Improved Balance Control" and filed February 24, 2016; which claims priority as a continuation of U.S. Patent 9,289,174, entitled "Sensory Prosthetic for Improved Balance Control," which issued on March 22, 2016; which claims priority as a continuation of U.S. Patent 9,402,580, entitled "Sensory Prosthetic for Improved Balance Control," which issued on August 2, 2016, which claims priority as a continuation of U.S. Patent 8,974,402, entitled "Sensory Prosthetic for Improved Balance Control," which issued on March 10, 2015, which was the U.S. national stage filing of PCT App. PCT/US03/11338, filed April 14, 2003 entitled "Sensory Prosthetic for Improved Balance Control," which claims priority to U.S. Patent Application 60/372,148, entitled "Sensor Prosthetic for Improved Balance Control" and filed April 12, 2002, all of which are hereby incorporated herein by reference in their entireties.--

Signed and Sealed this
Seventeenth Day of November, 2020

Andrei Iancu
*Director of the United States Patent and Trademark Office*